United States Patent
Enholm et al.

(10) Patent No.: US 9,962,563 B2
(45) Date of Patent: May 8, 2018

(54) ENERGY DENSITY MAP CALCULATING USING A THERMO ACOUSTIC MODE

(71) Applicant: KONINKLIJKE PHILIPS N.V., Eindhoven (NL)

(72) Inventors: Julia Kristina Enholm, Helsingfors (FI); Kirsi Ilona Nurmilaukas, Vantaa (FI); Max Köhler, Espoo (FI)

(73) Assignee: KONINKLIJKE PHILIPS N.V. (NL)

( * ) Notice: Subject to any disclaimer, the term of this patent is extended or adjusted under 35 U.S.C. 154(b) by 0 days. days.

(21) Appl. No.: 14/387,630

(22) PCT Filed: Mar. 22, 2013

(86) PCT No.: PCT/IB2013/052270
§ 371 (c)(1),
(2) Date: Sep. 24, 2014

(87) PCT Pub. No.: WO2013/150409
PCT Pub. Date: Oct. 10, 2013

(65) Prior Publication Data
US 2015/0065921 A1  Mar. 5, 2015

Related U.S. Application Data

(60) Provisional application No. 61/619,581, filed on Apr. 3, 2012.

(51) Int. Cl.
*A61H 1/00* (2006.01)
*A61N 7/02* (2006.01)
(Continued)

(52) U.S. Cl.
CPC ................ *A61N 7/02* (2013.01); *A61B 18/18* (2013.01); *A61B 18/1815* (2013.01);
(Continued)

(58) Field of Classification Search
CPC .................................... A61N 7/02; A61N 7/00
See application file for complete search history.

(56) References Cited

U.S. PATENT DOCUMENTS

| 6,386,278 | B1 | 5/2002 | Schulz-Harder |
| 2007/0106157 | A1 | 5/2007 | Kaczkowski |
| 2007/0232932 | A1* | 10/2007 | Palmer ................ A61B 5/0071 600/476 |
| 2008/0275330 | A1 | 11/2008 | Mu et al. |

(Continued)

FOREIGN PATENT DOCUMENTS

| CN | 201667332 U | 12/2010 |
| EP | 2500740 A1 | 9/2012 |

(Continued)

*Primary Examiner* — Hien Nguyen

(57) ABSTRACT

A medical apparatus (300, 400, 500, 600, 700) comprises a heating system (304) for heating a target zone (324) of a subject (320), wherein the energy density in a predefined volume is modeled (338) using a thermal model and a processor (330) for controlling (340) the heating system (304). The medical apparatus (300, 400, 500, 600, 700) further comprises a memory (336) containing machine executable instructions, wherein execution of the instructions causes the processor (330) to receive (100, 200, 342) a treatment plan, wherein execution of the instructions further causes the processor (330) to repeatedly: heat (102, 202, 344) the target zone (324) during alternating heating periods and cooling periods by controlling (340) the heating system (304) using the treatment plan and calculate (104, 204, 346) a present energy density map (350) in a predefined volume using the treatment plan and the thermal model, wherein the present energy density is repeatedly updated (348) during the heating of the target zone (324).

11 Claims, 8 Drawing Sheets

(51) Int. Cl.
    *A61B 18/18*     (2006.01)
    *A61B 18/20*     (2006.01)
    *A61F 7/00*     (2006.01)
    *A61N 5/00*     (2006.01)
    *A61B 90/00*     (2016.01)
    *A61B 18/14*     (2006.01)
    *A61B 18/00*     (2006.01)
    *A61B 34/10*     (2016.01)

(52) U.S. Cl.
    CPC .............. *A61B 18/20* (2013.01); *A61B 34/10* (2016.02); *A61B 90/36* (2016.02); *A61F 7/00* (2013.01); *A61N 5/00* (2013.01); *A61B 18/14* (2013.01); *A61B 2018/00577* (2013.01); *A61B 2018/00803* (2013.01); *A61B 2018/1807* (2013.01); *A61B 2034/101* (2016.02); *A61B 2090/374* (2016.02)

(56) References Cited

U.S. PATENT DOCUMENTS

| | | |
|---|---|---|
| 2009/0326420 A1* | 12/2009 | Moonen ............ A61N 7/02 601/3 |
| 2010/0106019 A1 | 4/2010 | Friemel |
| 2010/0208965 A1* | 8/2010 | Jiang ............ A61B 5/0073 382/131 |
| 2011/0060221 A1 | 3/2011 | Fan |
| 2011/0313329 A1 | 12/2011 | Koehler |
| 2014/0012155 A1 | 1/2014 | Flaherty et al. |

FOREIGN PATENT DOCUMENTS

| | | |
|---|---|---|
| JP | 2004358264 A | 12/2004 |
| WO | 2007047247 A1 | 4/2007 |
| WO | 2010029479 A1 | 3/2010 |
| WO | 2011080631 A2 | 7/2011 |

\* cited by examiner

ENERGY DENSITY MAP CALCULATING USING A THERMO ACOUSTIC MODE

CROSS-REFERENCE TO PRIOR APPLICATIONS

This application is the U.S. National Phase application under 35 U.S.C. § 371 of International Application No. PCT/IB2013/052270, filed on Mar. 22, 2013, which claims the benefit of U.S. Provisional Patent Application No. 61/619,581, filed on Apr. 3, 2012. These applications are hereby incorporated by reference herein.

TECHNICAL FIELD

The invention relates to a heating system for heating a target zone using a treatment plan and an energy density map calculation using a thermo acoustic model.

BACKGROUND OF THE INVENTION

Ultrasound from a focused ultrasonic transducer can be used to selectively treat regions inside a subject. Ultrasonic waves are transmitted as high energy mechanical vibrations. These vibrations induce tissue heating as they are damped, and they can also lead to cavitation. Both tissue heating and cavitation can be used to destroy tissue in a clinical setting. However, heating tissue with ultrasound is easier to control than cavitation. Ultrasonic treatments can be used to ablate tissue and to destroy regions of cancer cells selectively. This technique has been applied to the treatment of uterine fibroids, and has reduced the need for hysterectomy procedures. At lower powers or in pulsed mode, ultrasound can be used to selectively deliver genetic material or medicine to a region.

To perform ultrasonic therapy, a focused ultrasonic transducer can be used to focus the ultrasound on a particular treatment volume. The transducer is typically mounted within a medium, such as degassed water, that is able to transmit ultrasound. Actuators are then used to adjust the position of the ultrasonic transducer and thereby adjust the tissue region that is being treated.

HIFU procedures in a clinical setting are typically image-guided to permit treatment planning and targeting before applying a therapeutic or ablative level of ultrasound energy. Usually MRI is used for image-guidance, but it is also possible to use ultrasonography.

United States patent application US 2011/0313329 defines a therapy system for depositing energy which has a feed forward control of the therapy module. Particularly, in this known therapy module the cooling down period is estimated on an a priori estimate on the induced heating.

SUMMARY OF THE INVENTION

The invention provides for a medical apparatus, a method, and a computer program product in the independent claims. Embodiments are given in the dependent claims.

The invention provides for a medical apparatus for using energy density data for safety, planning and treatment time optimization in high intensity focused ultrasound. The applied energy density in the treatment volume is saved for each sonication so that the cumulative energy density can be assessed and used for safety checking, i.e., limiting the maximum cumulative energy density at any location, planning the position of the next treatment and for visual assessment of local energy deposition.

A 'processor' as used herein encompasses an electronic component which is able to execute a program or machine executable instruction. The processor may for instance be a multi-core processor. A processor may also refer to a collection of processors within a single computer system or distributed amongst multiple computer systems. Many programs have their instructions performed by multiple processors that may be within the same computing device or which may even be distributed across multiple computing devices.

'Computer memory' or 'memory' is an example of a computer-readable storage medium. Computer memory is any memory which is directly accessible to a processor. Examples of computer memory include, but are not limited to: RAM memory, registers, and register files.

'Computer storage' or 'storage' is an example of a computer-readable storage medium. Computer storage is any non-volatile computer-readable storage medium. Examples of computer storage include, but are not limited to: a hard disk drive, a USB thumb drive, a floppy drive, a smart card, a DVD, a CD-ROM, and a solid state hard drive. In some embodiments computer storage may also be computer memory or vice versa.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer to indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen.

Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

In one aspect the invention provides for a medical apparatus comprising a heating system for heating a target zone of a subject and a processor for controlling the heating system. The medical apparatus further comprises a memory containing machine executable instructions, wherein execution of the instructions causes the processor to receive a treatment plan, wherein execution of the instructions further causes the processor to repeatedly: heat the target zone during alternating heating periods and cooling periods by controlling the heating system using the treatment plan, calculate a present energy density map in a predefined volume using the treatment plan and a thermo acoustic model, wherein the present energy density is repeatedly updated during the heating of the target zone and update the treatment plan using the present energy density map.

A heating system as used herein encompasses a system for locally heating a portion of the subject. A treatment plan as used herein may encompass a plan or machine controls developed by a physician or other medical professional which are descriptive of the controls that can be used to generate such controls to control the heating system to heat a target zone within the subject. A thermo acoustic model as used herein combines acoustic and thermal parameters to obtain a possibly more accurate model of the heating as well as cool down.

The estimation for the induced heating, off focus and/or in the target zone, and/or the cool-down periods are made on the basis of a thermal model. The thermal model represents the thermal perfusion and diffusion, i. e. the transport of heat through the tissue. The thermal model used for simulation requires the intensity distribution as input in addition to other thermal parameters. The in vivo intensity distribution may in turn be calculated based on a multilayer tissue model. The multilayered tissue model may in turn be acquired based on the treatment plan. The acoustic and thermal parameters may be determined for each layer either based on knowledge and/or refined based on the heating thereby improving the accuracy of the estimate even further. The simulations may also be beneficial to estimate the focal region heating before initiating the heat deposition. According to the invention the cool-down period is chosen so that the tissue is expected to have cooled down to a predefined temperature before starting the next heating.

In one embodiment the execution of the instructions further causes the processor to calculate a cumulative energy density map by using weighted averaging to calculate the cumulative energy density maps taking into account estimated rate of tissue cooling and to display the cumulative energy density map on a display. The cumulative energy density map can also be calculated by summing the repeatedly calculated present energy density maps taking into account estimated rate of tissue cooling. A plain summation would also constitute a sort of weighted averaging.

A cumulative energy density map as used herein encompasses the assessment of cumulative thermal effects and this map can be shown to the user to indicate the best location of the next sonication.

This embodiment is particularly advantageous because it may allow for optimization of the entire treatment time, since the next treatment is always chosen in such a way that the required cool-down time is minimized.

In another embodiment the execution of the instructions further causes the processor to modify the treatment plan in accordance with the cumulative energy density map taking into account a next heating event.

This embodiment is particularly advantageous because it may allow finding the position for the target zone that is the safest and with the shortest cool-down time, wherein the system could automatically indicate the most suitable or most dangerous locations to the user. And this embodiment may allow for optimization of the treatment time and protection of the healthy tissue. The most dangerous locations as used herein are locations outside the target volume with a high temperature, i.e, the cool-down period was too short. On the other hand the most suitable locations are a location in which the cool-down was sufficient or no formerly heating takes place.

In another embodiment the execution of the instructions causes the processor to determine a safe power level map using the cumulative energy density map and to display the safe power level map on a display.

This embodiment may be advantageous because it protects the tissue by avoiding skin burn because only locations that are "safe" were heated again. Also subcutaneous fat sclerosis can be minimized with this embodiment. It should be noted that the "safe power level" depends heavily on the expected duration of the sonication to be performed. The reason is that the near field heating depends largely on the energy, i.e., the product of the power and sonication duration.

In another embodiment the execution of the instructions further causes the processor to halt the heating of the target zone if at least a portion of the cumulative energy density map is above a predetermined heating threshold.

This embodiment may be advantageous because it further protects the healthy tissue.

In another embodiment the medical apparatus further comprises a magnetic resonance imaging system comprising a magnet with an imaging zone, wherein the magnetic resonance imaging system is operable for acquiring thermal magnetic resonance data from a target zone within the imaging zone, wherein execution of the instructions further cause the processor to repeatedly acquire the thermal magnetic resonance data using the magnetic resonance imaging system and to determine a thermal map of the predefined volume using the thermal magnetic resonance data.

This embodiment may be advantageous because using the temperature rise in such locations that are monitored may help to calibrate the energy density map.

In another embodiment the execution of the instructions further causes the processor to halt the heating of the target zone if at least a portion of the thermal map is above a predetermined temperature.

According to the above mentioned advantages this embodiment further protects the healthy tissue.

In another embodiment the execution of the instructions further causes the processor to validate the thermo acoustic model using the thermal data.

In another embodiment the execution of the instructions further causes the processor to combine thermal data from within the imaging zone with cumulative energy density data to get an assessment of actual temperature in target zones both within and outside the imaging zone.

This embodiment is particularly advantageous because it may be used to calculate the temperature to assist in planning the next treatment to find the locations that have the least previous thermal build-up.

In another embodiment the predefined volume is at least partially outside of the target zone.

In another embodiment the heating system is any one of the following: high intensity focused ultrasound, radio-frequency heating system, a microwave ablation system, a hyperthermia therapy system, a laser ablation system, and an infrared ablation system.

In another aspect the invention provides for a computer implemented method of operating a medical apparatus, wherein the medical apparatus comprises a heating system for heating a target zone of a subject, wherein the method comprises receiving a treatment plan by the heating system and repeatedly heating the target zone during alternating heating periods and cooling periods by controlling the heating system using the treatment plan, calculating a present energy density map in a predefined volume using the treatment plan and a thermo acoustic model, wherein the present energy density is repeatedly updated during the heating of the target zone and updating the treatment plan using the present energy density map.

In another aspect the invention provides for a computer program product comprising machine executable instructions for execution by a processor controlling a medical apparatus, wherein the medical apparatus comprises a heating system for heating a target zone of a subject, wherein execution of the instructions causes the processor to receive a treatment plan, wherein execution of the instructions further causes the processor to repeatedly heat the target zone during alternating heating periods and cooling periods by controlling the heating system using the treatment plan, calculate a present energy density map in a predefined volume using the treatment plan and a thermo acoustic model, wherein the present energy density is repeatedly updated during the heating of the target zone and update the treatment plan using the present energy density map.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
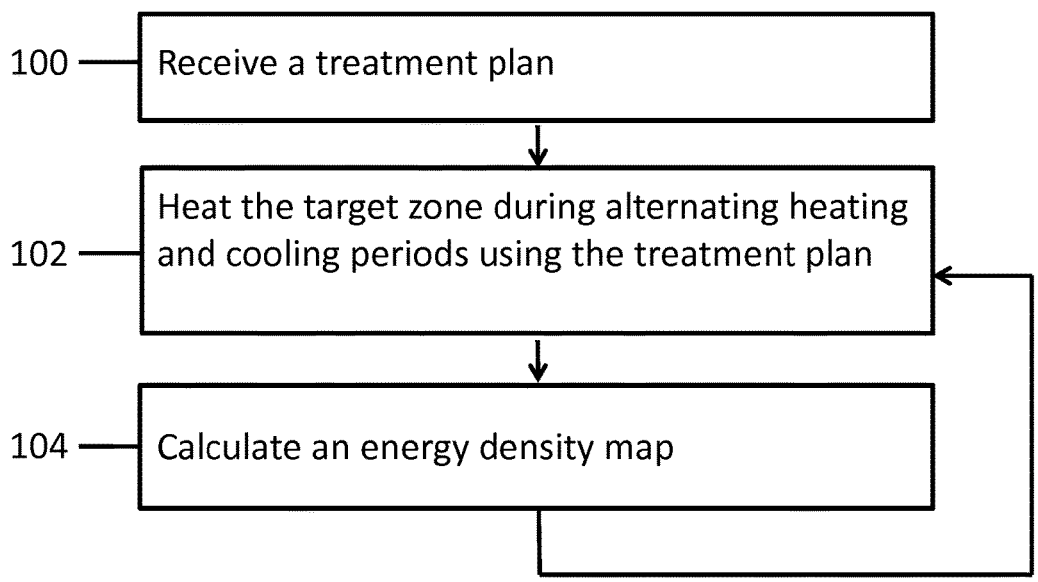
FIG. 1 shows a flow diagram which illustrates the method according to an embodiment of the invention.

FIG. 1 shows a flow diagram which illustrates the method according to an embodiment of the invention. In step 100 a treatment plan is received by using a thermal model. In step 102 the target zone is heated during alternating heating and cooling periods using the treatment plan. Finally in step 104 an energy density map in a predefined volume is calculated by using the treatment plan. The energy density map is repeatedly updated during the heating of the target zone. The steps 102 and 104 can be repeated several times.

Figure 2:
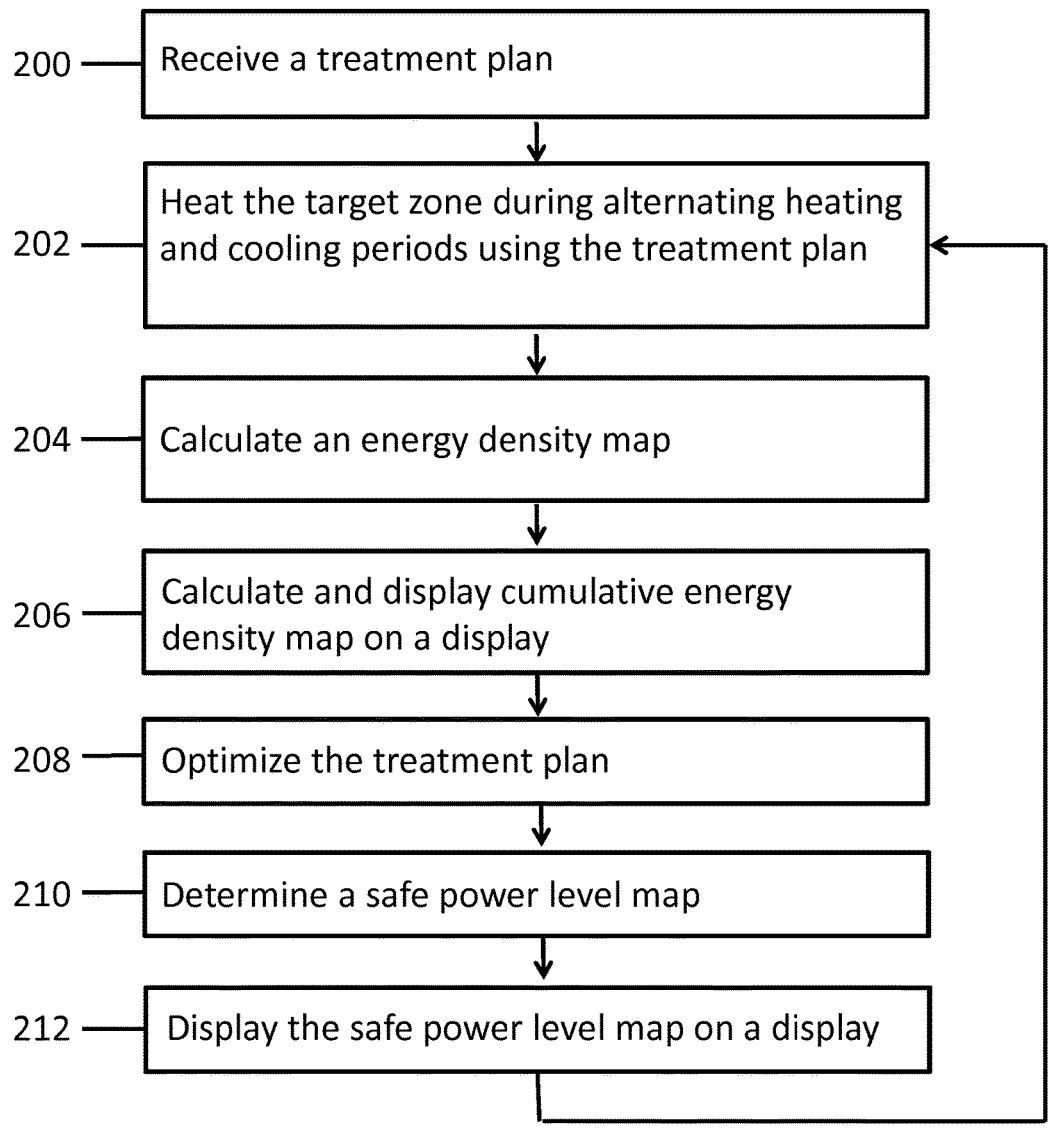
FIG. 2 shows a flow diagram which shows a further embodiment of a method according to an embodiment of the invention.

FIG. 2 shows a flow diagram which shows a further embodiment of a method according to an embodiment of the invention. Steps 200-204 correspond to steps 100-104 of FIG. 1. In step 200 a treatment plan is received by using a thermal model. In step 202 the target zone is heated during alternating heating and cooling periods using the treatment plan. In step 204 an energy density map in a predefined volume is calculated by using the treatment plan. In step 206 a cumulative energy density map in a predefined volume is calculated and displayed on a display. Then the treatment plan is optimized in step 208 by using the cumulative energy density map from step 206. In step 210 a safe power level map is determined by using the cumulative energy density map according to step 206. Finally, the safe power level map is displayed on a display, which is step 212. The steps 202 and 212 can be repeated several times.

Figure 3:
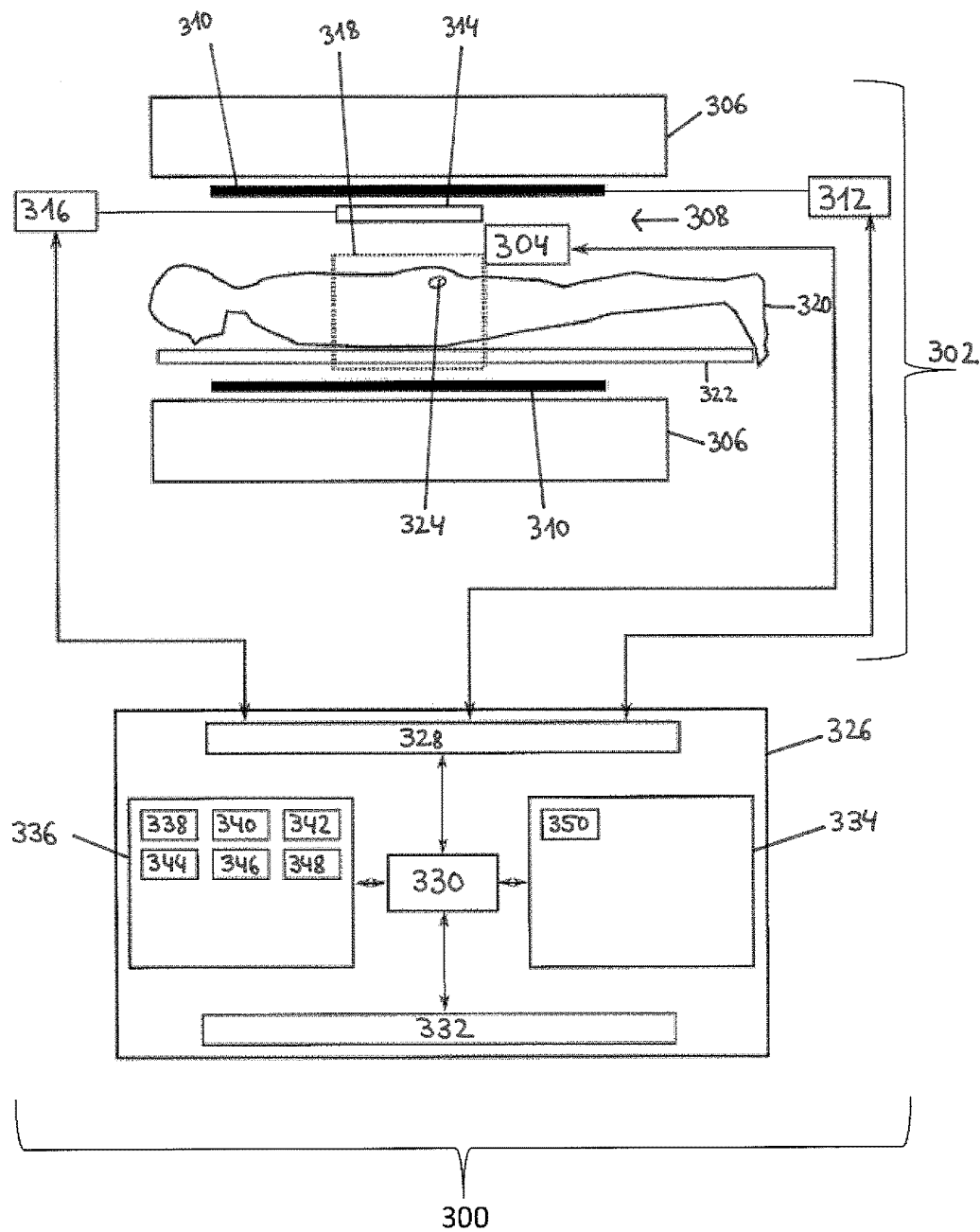
FIG. 3 illustrates a medical apparatus according to an embodiment of the invention.

FIG. 3 illustrates a medical apparatus 300 according to an embodiment of the invention. The medical apparatus 300 comprises a magnetic resonance imaging system 302. The magnetic resonance imaging system 302 is shown as comprising a magnet 306. The magnet 306 is a cylindrical type superconducting magnet with a bore 308 through the center of it. The magnet 306 has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone 318 where the magnetic field is strong and uniform enough to perform magnetic resonance imaging.

Also within the bore of the magnet is a magnetic field gradient coil 310 which is used for acquisition of magnetic resonance data to spatially encode magnetic spins within an imaging zone 318 of the magnet 306. The magnetic field gradient coil 310 is connected to a magnetic field gradient coil power supply 312. The magnetic field gradient coil 310 is representative. Typically magnetic field gradient coils 310 contain three separate sets of coils for spatially encoding in three orthogonal spatial directions. A magnetic field gradient power supply 312 supplies current to the magnetic field gradient coils 310. The current supplied to the magnetic field coils is controlled as a function of time and may be ramped and/or pulsed.

Adjacent the imaging zone 318 is a radio-frequency coil 314. The radio-frequency coil 314 is connected to a radio-frequency transceiver 316. Also within the bore of the magnet 306 is a subject 320 that is reposing on a subject support 322 and is partially within the imaging zone 318.

Adjacent to the imaging zone 318 is a radio-frequency coil 314 for manipulating the orientations of magnetic spins within the imaging zone 318 and for receiving radio transmissions from spins also within the imaging zone 318. The radio-frequency coil 314 may contain multiple coil elements. The radio-frequency coil 314 may also be referred to as a channel or an antenna. The radio-frequency coil 314 is connected to a radio frequency transceiver 316. The radio-frequency coil 314 and the radio frequency transceiver 316 may be replaced by separate transmit and receive coils and a separate transmitter and receiver. It is understood that the radio-frequency coil 314 and the radio-frequency transceiver 316 are representative. The radio-frequency coil 314 is intended to also represent a dedicated transmit antenna and a dedicated receive antenna. Likewise the transceiver 316 may also represent a separate transmitter and a separate receiver.

The magnetic field gradient coil power supply 312 and the radio-frequency transceiver 316 are connected to a hardware interface 328 of a computer system 326. The computer system 326 further comprises a processor 330. The processor 330 is connected to the hardware interface 328. The hardware interface 328 enables the processor 330 to send and receive data and commands to the magnetic resonance imaging system 302. The computer system 326 further comprises a user interface 332, computer storage 334 and computer memory 336.

In this case a heating system 304 has been incorporated into the medical apparatus 300. The heating system 304 was connected to the hardware interface 328 of the computer system 326 and is operable for being controlled by the processor 330. The heating system 304 in this embodiment is intended to be generic and may represent any system used for heating a portion of a subject. The heating system 304 may for instance be a high-intensity focused ultrasound system, a radio-frequency heating system, a microwave ablation system, a hyperthermia therapy system, a laser ablation system, and an infrared ablation system.

The computer memory 336 is shown as containing a thermal model modeling module 338. The thermal model modeling module 338 contains computer executable code which enables the heating system 304 to model the energy density in a predefined volume using a thermal model. The computer storage 334 further contains a heating system controlling module 340 which enables the processor 330 to control the heating system 304. Furthermore, the computer storage 334 contains a treatment plan receiving module 342. The treatment plan receiving module 342 contains computer executable code which enables the processor 330 to receive 100, 200 a treatment plan. The target zone heating module 344 contains computer executable code which enables the processor 330 to heat 102, 202 the target zone 324 during alternating heating periods and cooling periods by controlling the heating system 304 using the heating system controlling module 340. And the computer memory 336 contains a density map calculating module 346 and a density map updating module 348. The density map calculating module 346 calculates a present energy density map in a predefined volume using the treatment plan and a thermo acoustic model, wherein the present energy density is repeatedly updated during the heating of the target zone 324 using the density map updating module 348.

The computer storage 334 is shown as containing a cumulative energy density map 350. The cumulative energy density map 350 is determined using the received 100, 200 treatment plan using the treatment plan receiving module 342 and the calculated 104, 204 present energy density map using the density map calculating module 346. The present energy density map is repeatedly updated during the heating 102, 202 of the target zone 324 with the result of a cumulative energy density map 350.

Figure 4:
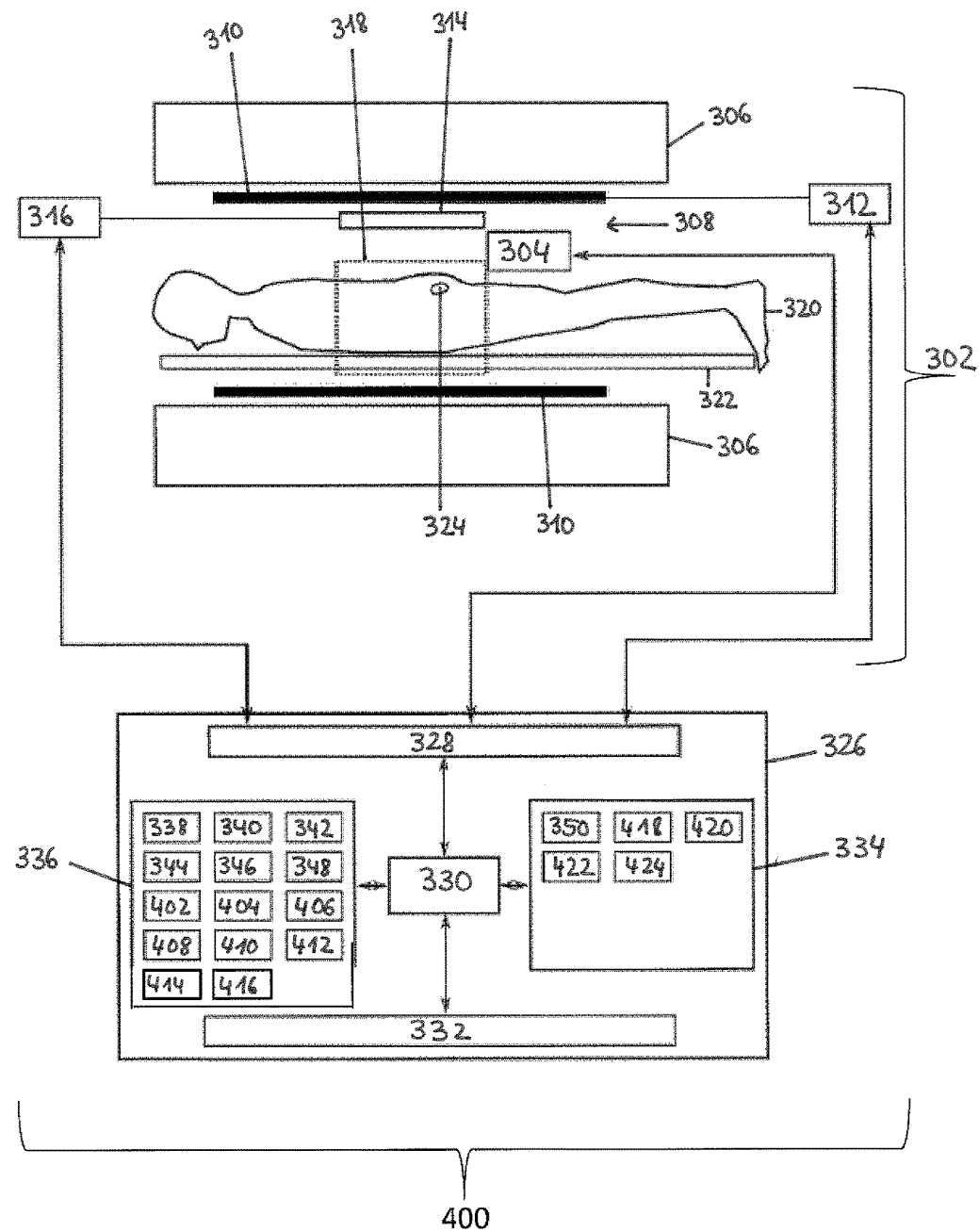
FIG. 4 shows a more detailed illustration of an embodiment of the invention shown in FIG. 3.

FIG. 4 illustrates a medical apparatus 400 according to a further embodiment of the invention. The embodiment shown in FIG. 4 is similar to that shown in FIG. 3. In addition to the features illustrated in FIG. 3 the medical apparatus 400 in FIG. 4 shows additional features in the computer storage 334 and the computer memory 336. The computer storage 334 is shown as additionally containing a safe power level map 418 and a thermal map 424. The computer storage 334 is also shown as containing magnetic resonance data 420 and magnetic resonance images 422. The magnetic resonance data 420 are acquired using the magnetic resonance imaging system 302.

The computer memory 336 is shown as additionally containing a density map displaying module 402. The density map displaying module 402 contains computer executable code which enables to display 206 the cumulative energy density map 350 on a display. Further the treatment plan optimizing module 404 contains computer executable code which enables the processor 330 to optimize 208 the treatment plan in accordance with the cumulative energy density map 350 taking into account both the history and the next heating event to find the position of the target zone 324 that is the safest and with the shortest cool-down-time, wherein the system could automatically indicate the most suitable or most dangerous locations to the user. The safe power level map 418 can be determined and displayed using the safe power level map determining module 406 and the safe power level map displaying module 408. The safe power level map determining module 406 contains computer executable code which enables the processor 330 to determine 210 a safe power level map 418 using the cumulative energy density map 350. And the safe power level map displaying module 408 contains computer executable code which enables the processor 330 to display 212 the safe power level map 418 on a display. Furthermore, the computer memory 336 contains a halting module 410. The halting module 410 contains computer executable code which enables the processor 330 to halt the heating of the target zone 324 if at least a portion of the cumulative energy density map 350 is above a predetermined heating threshold or if at least a portion of the thermal map 424 is above a predetermined temperature. Furthermore the computer memory 336 contains a thermal map determining module 412 which contains computer executable code which enables the processor 330 to determine a thermal map 424 of the predefined volume using the thermal magnetic resonance data 420. To validate the thermo acoustic model the computer memory 336 contains a thermo acoustic model validating module 414. The computer memory 336 further contains a data combining module 416 which contains computer executable code which enables the processor 330 to combine thermal data from within the imaging zone 318 with cumulative energy density data 350 to get an assessment of actual temperature in target zones 324 both within and outside the imaging zone 318.

Figure 5:
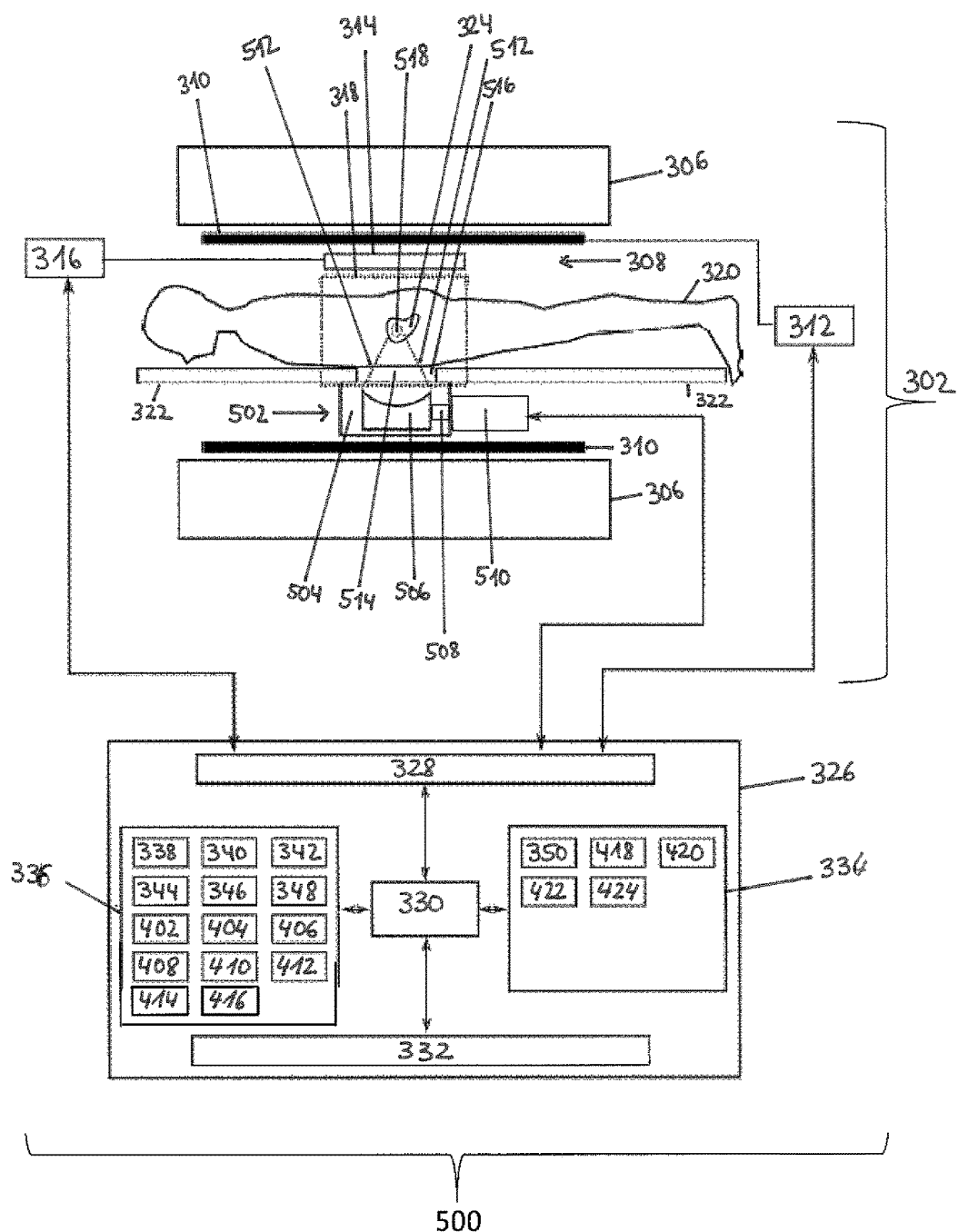
FIG. 5 illustrates a medical apparatus with an high-intensity focused ultrasound system according to an embodiment of the invention.

FIG. 5 shows a further embodiment of the medical apparatus 500 according to the invention. In this embodiment the heating system is a high-intensity focused ultrasound system 502. The high-intensity focused ultrasound system 502 comprises a fluid-filled chamber 504. Within the fluid-filled chamber 504 is an ultrasound transducer 506.

Although it is not shown in this FIG. the ultrasound transducer 506 may comprise multiple ultrasound transducer elements each capable of generating an individual beam of ultrasound. This may be used to steer the location of a sonication point 518 electronically by controlling the phase and/or amplitude of alternating electrical current supplied to each of the ultrasound transducer elements. The sonication point 518 is operable to be controlled to sonicate the target zone 324.

The ultrasound transducer 506 is connected to a mechanism 508 which allows the ultrasound transducer 506 to be repositioned mechanically. The mechanism 508 is connected to a mechanical actuator 510 which is adapted for actuating the mechanism 508. The mechanical actuator 510 also represents a power supply for supplying electrical power to the ultrasound transducer 506. In some embodiments the power supply may control the phase and/or amplitude of electrical power to individual ultrasound transducer elements. In some embodiments the mechanical actuator/power supply 510 is located outside of the bore 308 of the magnet 306.

The ultrasound transducer 506 generates ultrasound which is shown as following the path 512. The ultrasound 512 goes through the fluid-filled chamber 504 and through an ultrasound window 514. In this embodiment the ultrasound then passes through a gel pad 516. The gel pad is not necessarily present in all embodiments but in this embodiment there is a recess in the subject support 322 for receiving a gel pad 516. The gel pad 516 helps couple ultrasonic power between the transducer 506 and the subject 320. After passing through the gel pad 516 the ultrasound 512 passes through the subject 320 and is focused to a sonication point 518. The sonication point 518 is being focused within a target zone 324. The sonication point 518 may be moved through a combination of mechanically positioning the ultrasonic transducer 506 and electronically steering the position of the sonication point 518 to treat the entire target zone 324.

The high-intensity focused ultrasound system 502 is shown as being also connected to the hardware interference 328 of the computer system 326. The computer system 326 and the contents of its storage 334 and memory 336 are equivalent to that as shown in FIG. 4.

Figure 6:
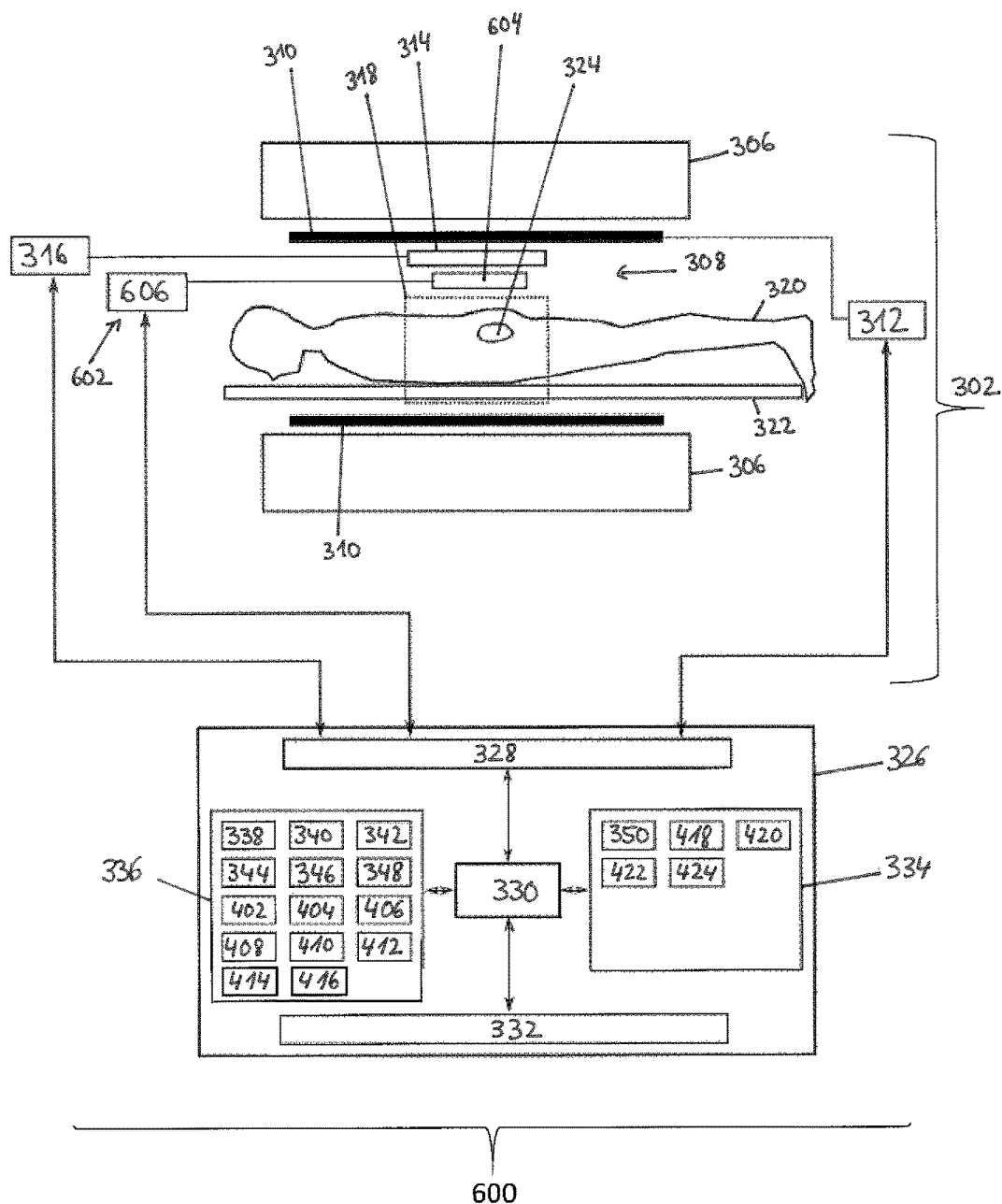
FIG. 6 illustrates a medical apparatus with a radio-frequency heating system according to an embodiment of the invention.

FIG. 6 illustrates a medical apparatus 600 according to a further embodiment of the invention. In this embodiment the heating system is a radio-frequency heating system 602. The embodiment shown in FIG. 6 is similar to that shown in FIGS. 3 and 4. The computer system 326 of FIG. 6 is equivalent to the computer system 326 shown in FIGS. 4 and 5. The contents of the computer storage 334 and the computer memory 336 are also equivalent to the computer storage 334 and the computer memory 336 as shown in FIGS. 4 and 5. In the embodiment shown in FIG. 6 a radio-frequency heating system 602 is used as the heating system. The radio-frequency heating system 602 comprises an antenna 604 and a radio-frequency transmitter 606. The antenna 604 is in the vicinity of target zone 324. Radio-frequency energy generated by the transmitter 606 and radiated by the antenna 604 is used to selectively heat the target zone 324. In this embodiment the radio-frequency transmitter 606 is shown as being connected to the hardware interface 328. The processor 330 and the contents of the computer storage 334 and the computer memory 336 are used to control the radio-frequency transmitter 606 in a manner equivalent to the way the high-intensity focused ultrasound system 502 of FIG. 5 is controlled by the processor 330.

Figure 7:
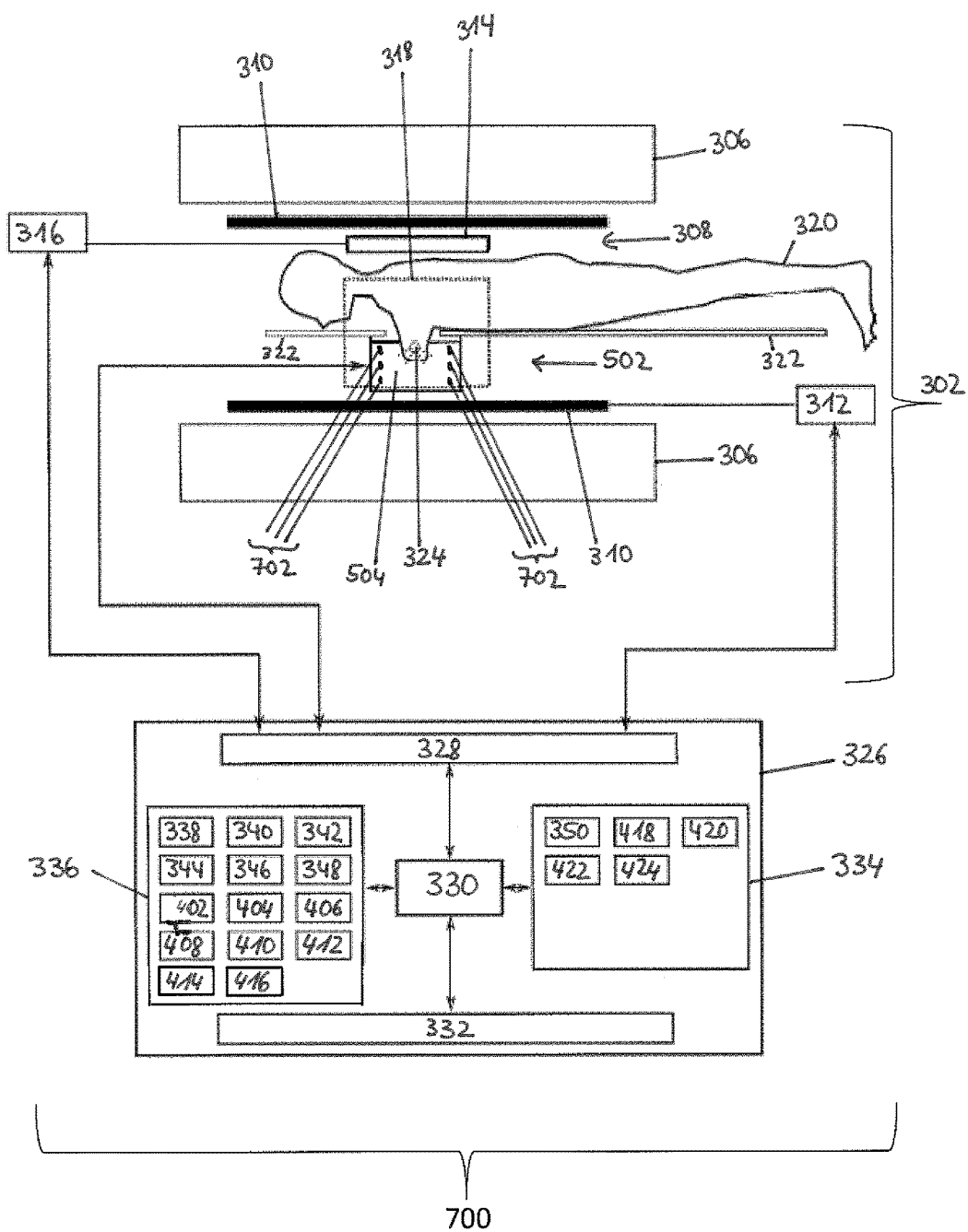
FIG. 7 illustrates a medical apparatus with another high-intensity focused ultrasound system according to an embodiment of the invention.

FIG. 7 illustrates a medical apparatus 700 according to a further embodiment of the invention. In this embodiment the heating system is a high-intensity focused ultrasound system 502 similar to that shown in FIG. 4. One difference to FIG. 4 is that the gel pad 416 is missing which enables that a portion of the subject 320 goes through an opening in the subject support 322. The portion extends and is partially surrounded by the ultrasound conducting fluid. In this example six ultrasonic transducer elements 702 are shown as being within the fluid-filled chamber 504. These transducer elements 702 are placed in a cylindrical order. The portion of the subject 320 in this case is a breast. There are two regions of tissue; there is a fat tissue region and a glandular tissue region. The path of ultrasound 512 goes from the ultrasonic transducer elements 702 through the fluid 504, through the fat tissue and through the glandular tissue to a sonication point 518 which is located within a target zone 324. The computer system 326 of FIG. 7 is equivalent to the computer system 326 shown in FIGS. 4, 5 and 6. The contents of the computer storage 334 and the computer memory 336 are also equivalent to the computer storage 334 and the computer memory 336 as shown in FIGS. 4, 5 and 6.

Figure 8:
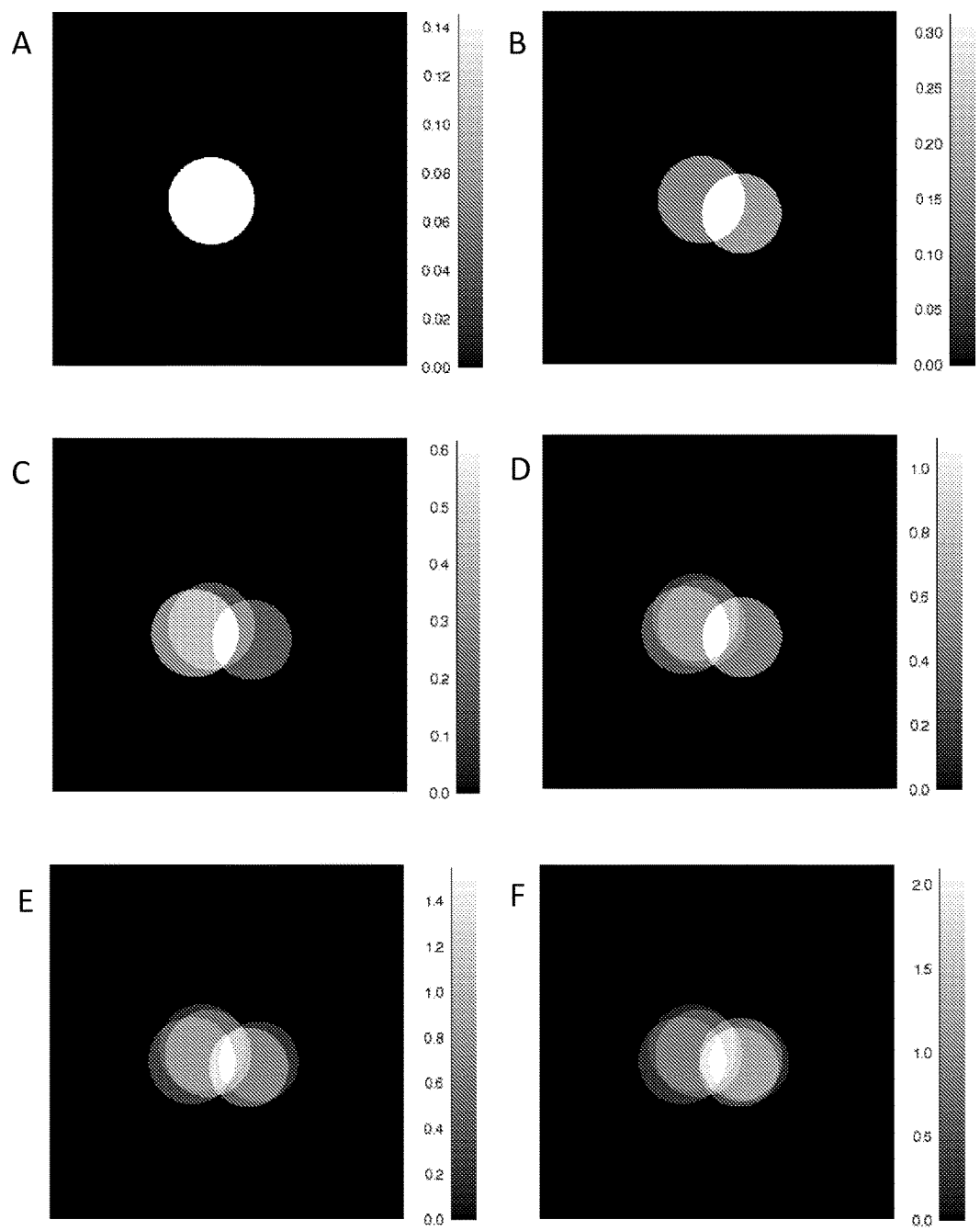
FIG. 8 shows an example of a cumulative energy density map of heating at the skin after 1, 2, 3, 5, 7 and 8 sonications.

FIG. 8 shows energy density maps representative of estimated heating at the skin after 1, 2, 3, 5, 7 and 8 sonications. The cumulative energy density map is calculated by summing the previous treatments and adding an estimate of the cool-down. This can be done by simply using a sliding window in time to include only the most recent treatments or by assuming for example exponential cool-down and assessing the cool-down time constant in the chosen location if some data on the cool-down properties of near-by structures exist. The images shown in FIG. 8 were done using a sliding window in time cool-down assessment method. The scale refers to $J/mm^2$ and the values differs for the different sonications. It means that the maximal density value grows with the number of sonications. FIG. 8A shows a energy density map after one sonication and consequently only one ring results. After two sonications, which is illustrated in FIG. 8B, the energy density map shows two rings and some parts are overlapping. In this overlapped area is the energy density higher than in the other areas. FIG. 8C-8F show the situation after more sonications (3, 5, 7 and 8). The with area is the area with the highest energy density and herein all sonications overlapped. Some areas indicated in different grey shapes are overlapped partly. So the conclusion of this is, that the brighter the area in the cumulative energy density map is the hotter the tissue will be. Alternatively, acoustic and thermal modeling can be applied using the beam shape and acoustic and thermal parameters to obtain a possibly more accurate model of the heating as well as cool down for each individual sonication as well as across a longer duration including several sonications but this is not shown in the FIG.

LIST OF REFERENCE NUMERALS 100-212 steps
300 medical apparatus
302 magnetic resonance imaging system
304 heating system
306 magnet
308 bore
310 magnetic field gradient coil
312 magnetic field gradient coil power supply
314 radio-frequency coil
316 transceiver 318 imaging zone
320 subject
322 subject support
324 target zone
326 computer system
328 hardware interface
330 processor
332 user interface
334 computer storage
336 computer memory
338 thermal model modeling module
340 heating system controlling module
342 treatment plan receiving module
344 target zone heating module
346 density map calculating module
348 density map updating module
350 cumulative energy density map
400 medical apparatus
402 density map displaying module
404 treatment plan optimizing module
406 safe power level map determining module
408 safe power level map displaying module
410 halting module
412 thermal map determining module
414 thermal acoustic model validating module
416 data combining module
418 safe power level map
420 magnetic resonance data
422 magnetic resonance image
424 thermal map
500 medical apparatus
502 high intensity focused ultrasound system
504 fluid-filled chamber
506 ultrasound transducer
508 mechanism
510 mechanical actuator/power supply
512 path of ultrasound
514 ultrasound window
516 gel pad
518 sonication point
600 medical apparatus
602 radio-frequency heating system
604 antenna
606 radio-frequency transmitter
700 medical apparatus
702 ultrasound transducer elements

The invention claimed is:

1. A medical apparatus comprising:
a heating system for heating a target zone of a subject;
a display device;
a processor for controlling the heating system;
a memory containing machine executable instructions, wherein execution of the instructions causes the processor to receive a treatment plan, wherein execution of the instructions further causes the processor to repeatedly:
control the heating system to heat the target zone during alternating heating periods and cooling periods using the received treatment plan;
calculate a present energy density map in a predefined volume using the treatment plan and a thermal model representing heat-transport through tissue, wherein the present energy density is repeatedly updated during the alternating heating periods and cooling periods of the target zone;
calculate a cumulative energy density map by summing the repeatedly updated calculated present energy density maps taking into account an estimated rate of tissue cooling based on the thermal model, wherein the cumulative energy density map comprises a visual map;
combine thermal magnetic resonance data from within an imaging zone with cumulative energy density data to get an assessment of actual temperature in the target zone;
control the display device to display the cumulative energy density map;
determine a next heating event location within the target zone using the cumulative energy density map, the next heating event location being a location with a shortest cooling period that does not thermally damage healthy tissue adjacent the target zone;
modify the treatment plan in accordance with the cumulative energy density map taking into account a next heating event; and
control the heating system to heat the next heating event location during the alternating heating periods and cooling periods using the modified treatment plan.

2. The medical apparatus of claim 1, wherein execution of the instructions causes the processor to:
determine a safe power level map using the cumulative energy density map; and
display the safe power level map on a display.

3. The medical apparatus of claim 1, wherein execution of the instructions further causes the processor to control the heating system to halt the heating of the target zone if at least a portion of the cumulative energy density map is above a predetermined heating threshold.

4. The medical apparatus of claim 1, wherein the medical apparatus further comprises a magnetic resonance imaging system comprising a magnet, wherein the magnetic resonance imaging system is operable for acquiring the thermal magnetic resonance data from a target zone within the imaging zone, wherein execution of the instructions further cause the processor to repeatedly:
acquire the thermal magnetic resonance data using the magnetic resonance imaging system; and
determine a thermal map of the predefined volume using the thermal magnetic resonance data.

5. The medical apparatus of claim 4, wherein execution of the instructions further causes the processor to control the heating system to halt the heating of the target zone if at least a portion of the thermal map is above a predetermined temperature.

6. The medical apparatus of claim 4, wherein execution of the instructions further causes the processor to validate the thermal model using the thermal magnetic resonance data.

7. The medical apparatus of claim 4, wherein the predefined volume is at least partially outside of the target zone.

8. The medical apparatus of claim 4, wherein the heating system is selected from a group consisting of a high intensity focused ultrasound, a radio-frequency heating system, a microwave ablation system, a hyperthermia therapy system, a laser ablation system, and an infrared ablation system.

9. A computer implemented method of operating a medical apparatus, wherein the medical apparatus comprises a heating system for heating a target zone of a subject, wherein the method comprises with an aid of a computer, repeatedly:
controlling the heating system to heat the target zone during alternating heating periods and cooling periods using a received treatment plan;
calculating a present energy density map in a predefined volume using the treatment plan and a thermal model representing heat transport through tissue, wherein the present energy density is repeatedly updated using the treatment plan and the thermal model during the alternating heating and cooling periods of the target zone;

calculating a cumulative energy density map by using weighted averaging of the present energy density maps taking into account an estimated rate of tissue cooling based on the thermal model, wherein the cumulative energy density map comprises a visual map;

combine thermal magnetic resonance data from within an imaging zone with cumulative energy density data to get an assessment of actual temperature in the target zone;

controlling a display to display the cumulative energy density map;

determining a next heating event location within the target zone using the cumulative energy density map;

modifying the treatment plan in accordance with the cumulative energy density map taking into account a next heating event; and controlling the heating system to perform the next heating event using a shortest cooling period that does not damage healthy tissue adjacent the target zone at the next event location in accordance with the modified treatment plan.

10. The method of claim 9, further including:

controlling a magnetic resonance imaging system to repeatedly generate a thermal map of a region of the subject including the target zone;

validate the thermal model using the thermal map.

11. A non-transitory computer program product comprising machine executable instructions for execution by a processor controlling a medical apparatus, wherein the medical apparatus comprises a heating system for heating a target zone of a subject, a display device, and a thermal imaging device, wherein execution of the instructions causes the processor to receive a treatment plan, wherein execution of the instructions further causes the processor to repeatedly:

control the heating system to heat the target zone during alternating heating periods and cooling periods using the treatment plan;

calculate a present energy density map in a predefined volume using the treatment plan and a thermal model representing heat transport properties of tissue of the subject, wherein the present energy density is repeatedly updated during the heating of the target zone, the heating including the alternating heating periods and cooling periods;

control the thermal imaging device to generate thermal images of a region of the subject including the target zone;

use the thermal images to determine and validate the thermal model;

calculate a cumulative energy density map by summing the repeatedly updated calculated the present energy density maps taking into account estimated rate of tissue cooling during the cooling periods based on the thermal model, wherein the cumulative energy density map comprises a visual map;

combine thermal magnetic resonance data from within an imaging zone with cumulative energy density data to get an assessment of actual temperature in the target zone;

control the display device to display the cumulative energy density map;

determine a next heating event location within the target zone using the cumulative energy density map;

modify the treatment plan in accordance with the cumulative energy density map taking into account a next heating event; and control the heating system to deliver the next heating event using a shortest cooling period that does not damage healthy tissue adjacent the target zone at the determined next heating event location using the modified treatment plan.

* * * * *